(12) United States Patent
Rosen

(10) Patent No.: US 7,235,265 B2
(45) Date of Patent: Jun. 26, 2007

(54) HERBAL SKIN FORMULATION

(76) Inventor: Ross Rosen, 166 Mountain Ave., Westfield, NJ (US) 07090

( * ) Notice: Subject to any disclaimer, the term of this patent is extended or adjusted under 35 U.S.C. 154(b) by 0 days.

(21) Appl. No.: 11/262,683

(22) Filed: Oct. 31, 2005

(65) Prior Publication Data
US 2007/0098669 A1    May 3, 2007

(51) Int. Cl.
*A61K 36/65*    (2006.01)
*A61K 36/232*   (2006.01)
*A61K 36/804*   (2006.01)

(52) U.S. Cl. ...................................... 424/725; 424/547
(58) Field of Classification Search ..................... None
See application file for complete search history.

(56) References Cited

OTHER PUBLICATIONS

Beksy and Gambel "Chinese Herbal Medicine Materia Medica" Eastland Press, pp. 71, 225, and 328.*

* cited by examiner

*Primary Examiner*—Susan Hoffman
(74) *Attorney, Agent, or Firm*—Edward M. Fink

(57) ABSTRACT

An herbal skin formulation is described which is obtained by mixing naturally occurring Chinese herbs in a cooking vessel, adding sesame oil and continuing cooking until the mixture is browned. The herbs are then removed and beeswax added to the sesame oil until melting occurs. Upon cooling, the resultant is poured into jars. Suitable formulations for different purposes are described.

8 Claims, No Drawings

HERBAL SKIN FORMULATION

FIELD OF THE INVENTION

This invention relates to a novel herbal skin formulation. More particularly, the present invention relates to a skin formulation comprising natural Chinese herbs which are selected for the purpose of addressing acute symptoms and promote healing of the skin.

BACKGROUND OF THE INVENTION

Chinese herbal medicine has been in use for many centuries and is frequently used in conjunction with acupuncture or independently. Practitioners of Chinese medicine view the notion of "balance" as the basis of their professional practice and they define the concept of health as the balance of yin and yang and the smooth flow of Qi (life force) throughout the body. An imbalance results in the malfunction of the body and ofttimes illness, the imbalance being caused by mental and emotional stress, improper diet, environmental factors, genetic predispositions, etc.

The practitioner begins study of an individual by means of as evaluation using diagnostic tools such as observation, listening and smelling, questioning and palpation. The information acquired is then used to formulate a pattern of health which ofttimes includes herbal therapies. Studies have shown that the use of these herbs tend to promote healing as opposed to Western medications which focus upon the masking of symptoms. Accordingly, numerous studies have been undertaken with the goal of obtaining novel herbal therapies which are suitable for treating skin disorders.

SUMMARY OF THE INVENTION

In accordance with the present invention, novel formulations of Chinese herbs have been prepared which results in the nourishing of the skin which moisten and invigorate the skin while enhancing blood circulation. More specifically, the present invention is directed to the formulation of a combination of Chinese herbs which have proven be useful for treatment of a wide range of skin disorders including eczema, psoriasis, dry skin, itching and the like.

DETAILED DESCRIPTION OF THE INVENTION

The unique combination of Chinese herbs chosen for use herein have been found to invigorate then skin as it penetrates beneath the skin to the fascia and muscles, thereby enhancing surface circulation while reducing stagnant energy and blood.

The primary ingredients of the novel herbal composition include Tang Kuei (dang gui) and prepared Rehmannia (shu di huang) which allow penetration into the fascia and the blood level to improve microcirculation, Amebia (zi cao), Polygonum (he shou wu) and Raw Rehmania (sheng di huang) which strengthen the blood and clean heat and toxins from the blood and skin layer, Mother of Pearl (zhen zhu mu), White Peony (bai shao) and Glehnia (sha shen) which moisten the skin, and Fructus Tribulus (bai ji li), Uncis Uncaria (gou teng) which treat itching and assist the other herbs in venting pathogens trapped in the skin and muscle layers. Sesame oil and Yellow beeswax complete the formulation. Each of the Chinese herbs alluded to herein is naturally occurring and may be found on the Chinese mainland as well as other locations throughout the world.

The chemical composition of each of the foregoing herbs is as follows:

Amebia—acetylshikonin, shikonin, alkannan, isobutlyrylshikonin, B-dimethylacryloylshikonin, B-hydroxyisovalerishikonin.

Tang Kuei—butylidene phthalide, ligustilide, n-butylidene-phthalide, sequiterpenes, carvacrol, dihyrophthalic anhydride, sucrose, vitamin B12, carotene, B-sitosterol.

Rehmania—B-sitosterol, manitol, stigmasterol, campesterol, rehmannin, catalpol, arginine, glucose.

Peony—paeoniflorin, paeonol, albiflorin, triterpenoids, sistosterol.

Uncaria—rhynchophllline, isorhynchophylline, corynoxeine, isocorynoxeine, corynantheine, nicotinic acid, hirsutine, hirsuteine.

Tribulus—kaempferol, kaempferol 3-glucoside, kaempferol 3-rutinside, tribuloside, harmine.

Polygonum—chrysophanic acid, emodin, rhein, chrysophanic acid anthrone, lecithin.

Mother of Pearl—calcium carbonate, magnesium carbonate, calcium phosphate, ferric oxide, silica, leucine, methioninie, alanine, glycine, glutamic acid, aspartic acid.

Giehnia—alkaloids

In preparing the novel formulations of the present invention, studies have revealed that the compositions which have proven to be most effective have included the following ingredients in an amount ranging from 2.5% to 50% based upon the total weight of the composition:

Dang Gui, Zi Cao Gen, Sha Shen, Gou Teng, Bai Shao, Sheng Di, Shu Di, He Shou Wu, Bai Ji Li, Zhen Zhu Mu together with sesame oil and soft Beeswax. A general preference has been found for the following composition:

Dang Gui—30 grams/12.5%
Zi Cao Gen—15 grams/6.25%
Sha Shen—30 grams/12.5%
Gou Teng—15 grams/6.25%
Bai Shou—30 grams/12.5%
Sheng Di—30 grams/12.5%
Shu Di—30 grams/12.5%
He Shou Wu—30 grams/12.5%
Bai Ju Li—15 grams/6.25%
Zhen Zhu Mu—15 grams/6.25%
Sesame Oil—750 ml.
Beeswax soft—12.5 grams or 90 grams hard Studies have shown that variations in the generic formulation set forth above may be made as follows to achieve the noted effect:

(a) To effect reduction in pain, the following ingredients are added to the formulation set forth above.
(1) Huo Xiang—2.5–50%
(2) Yan Hu Suo—2.5–50%
(3) Ru Xiang—2.5–50%
(4) Mo Yao—2.5 to 50%
(5) Tao Ren—2.5–50%
(6) Hong Hua—2.5
(b) to alleviate skin inflammation
(1) Chi Shao—2.5–50%
(2) Hong Hua—2.5–50%
(3) Qing Dai—2.5–50%
(4) Lavendar essential oil 5 drops 2.5–50-%
(c) to treat a rash with incomplete resolution
(1) Jing Jie—2.5–50%
(2) Fang Feng—2.5–50%
(3) Sheng Ma—2.5–50%
(4) Bo He—2.5–50%
(d) to treat weeping/oozing skin
(1) Ku Shen—2.5–50%

(2) Huo Xiang—2.5–50%
(3) Yi Yi Ren—2.5–50%
(4) Cang Zhu—2.5–50%
(5) Bai Zhu—2.5–50%
(6) Qing Dai—2.5–50%
(7) Huang Bai—2.5–50%
(8) Da Huang—2.5–50%
(9) Huang Lian—2.5–50%
(e) to treat skin burns
(1) Qing Dai—2.5–50%
(2) Di Yu—2.5–50%
(3) Ce Bai Ye—2.5–50%
(4) Dai Ji—2.5–50%
(5) Bai Ji—2.5–50%
(f) to treat open skin wounds, raw lesions and the like
(1) San Qi—2.5–50%
(2) Bai Ji—2.5–50%
(3) Di Yu—2.5–50%
(4) Da Ji—2.5–50%

In preparing the compositions described herein, all of the naturally occurring Chinese herbs in the described proportions are mixed together in a large cooking vessel selected from among ceramic, glass or clay. Metals such as aluminum and the like should not be used for this purpose. After mixing the herbs thoroughly, the sesame oil is added and the ingredients cooked until browned. Upon browning, the herbs are removed and the beeswax added to the sesame oil until it melts evenly. Following, the mixture is poured into glass jars, permitted to cool and harden.

As noted above, the formulations described herein may be used by herbal medicine practitioners in treating various skin ailments such as eczema, psoriasis, dry itching skin, burns pain and neuropathies and acne scars. Additionally, individuals having sensitive skin in a massage setting have been found to benefit from use of the described formulations. Skin allergies, rashes, eczema and psoriasis victims have been treated with the described formulations with a high degree of success. The formulations have also evidenced dramatic clinical success in treating patients undergoing radiation therapy. In such cases, it has been found that the formulations prevent radiation burns and alleviate pre-existing burns due to radiation. Application of the formulation two to three times a day has proven to be highly beneficial.

While the invention has been described in detail in the foregoing description, it will be understood by those skilled in the art that variations may be made without departing from the spirit and scope of the invention.

What is claimed is:

1. Herbal skin formulation comprising the following ingredients in an amount ranging from 2.5% to 50% based upon the total weight of the composition:
    Dang Gui, Zi Cao Gen, Sha Shen, Gou Teng, Bai Shao, Sheng Di, Shu Di, He Shou Wu, Bai Ji Li, Zhen Zhu Mu together with sesame oil and soft Beeswax.

2. Herbal skin formulation in accordance with claim 1 further comprising by weight of the total composition
    Huo Xiang—2.5–50%
    Yan Hu Suo—2.5–50%
    Ru Xiang—2.5–50%
    Mo Yao—2.5 to 50%
    Tao Ren—2.5–50%
    Hong Hua—2.5–50%.

3. Herbal skin formulation in accordance with claim 1 further comprising by weight of the total composition
    Chi Shao—2.5–50%
    Hong Hua—2.5–50%
    Qing Dai—2.5–50%
    Lavendar essential oil—2.5–50%.

4. Herbal skin formulation in accordance with claim 1 further comprising by weight of the total composition
    Jing Jie—2.5–50%
    Fang Feng—2.5–50%
    Sheng Ma—2.5–50%
    Bo He—2.5–50%.

5. Herbal skin formulation in accordance with claim 1 further comprising by weight of the total composition
    Ku Shen—2.5–50%
    Huo Xiang—2.5–50%
    Yi Yi Ren—2.5–50%
    Cang Zhu—2.5–50%
    Bai Zhu—2.5–50%
    Qing Dai—2.5–50%
    Huang Bai—2.5–50%
    Da Huang—2.5–50%
    Huang Lian—2.5–50%.

6. Herbal skin formulation in accordance with claim 1 further comprising by weight of the total composition
    Qing Dai—2.5–50%
    Di Yu—2.5–50%
    Ce Bai Ye—2.5–50%
    Dai Ji—2.5–50%
    Bai Ji—2.5–50%.

7. Herbal skin formulation in accordance with claim 1 further comprising by weight of the total composition
    San Qi—2.5–50%
    Bai Ji—2.5–50%
    Di Yu—2.5–50%
    Da Ji—2.5–50%.

8. Herbal skin formulation comprising
    Dang Gui—30 grams/12.5%
    Zi Cao Gen—15 grams/6.25%
    Sha Shen—30 grams/12.5%
    Gou Teng—15 grams/6.25%
    Bai Shou—30 grams/12.5%
    Sheng Di—30 grams/12.5%
    Shu Di—30 grams/12.5%
    He Shou Wu—30 grams/12.5%
    Bai Ji Li—15 grams/6.25%
    Zhen Zhu Mu—15 grams/6.25%
    Sesame Oil—750 ml.
    Beeswax soft—12.5 grams.

* * * * *